(12) United States Patent
Chornenky et al.

(10) Patent No.: US 11,571,560 B2
(45) Date of Patent: Feb. 7, 2023

(54) METHOD AND APPARATUS FOR CANCER TREATMENT

(71) Applicant: Minnesota Medical Physics LLC, Eden Prairie, MN (US)

(72) Inventors: Victor I. Chornenky, Minnetonka, MN (US); Ali Jaafar, Eden Prairie, MN (US)

(73) Assignee: Minnesota Medical Physics LLC, Eden Prairie, MN (US)

( * ) Notice: Subject to any disclaimer, the term of this patent is extended or adjusted under 35 U.S.C. 154(b) by 0 days.

(21) Appl. No.: 17/061,326

(22) Filed: Oct. 1, 2020

(65) Prior Publication Data

US 2022/0105341 A1    Apr. 7, 2022

(51) Int. Cl.
  *A61N 1/04*    (2006.01)
  *A61N 1/36*    (2006.01)
  *A61N 1/40*    (2006.01)

(52) U.S. Cl.
  CPC ....... *A61N 1/0472* (2013.01); *A61N 1/36002* (2017.08); *A61N 1/40* (2013.01)

(58) Field of Classification Search
  CPC ............. A61N 1/047; A61N 1/36; A61N 1/40
  See application file for complete search history.

(56) References Cited

U.S. PATENT DOCUMENTS

| | | |
|---|---|---|
| 9,486,638 B2 | 11/2016 | Chornenky |
| 9,884,199 B2 | 2/2018 | Chornenky et al. |
| 11,129,999 B2 | 9/2021 | Chornenky et al. |
| 2011/0065976 A1* | 3/2011 | Chornenky .............. A61N 2/02 600/14 |
| 2016/0038753 A1* | 2/2016 | Chornenky ............ A61N 2/002 600/14 |
| 2019/0299018 A1 | 10/2019 | Chornenky et al. |
| 2019/0299019 A1 | 10/2019 | Chornenky et al. |
| 2019/0299020 A1 | 10/2019 | Chornenky et al. |

FOREIGN PATENT DOCUMENTS

CN    213285361 U   *   5/2021

OTHER PUBLICATIONS

English Translation of CN21328536 (Year: 2021).*

* cited by examiner

*Primary Examiner* — Allen Porter
*Assistant Examiner* — Adreanne A. Arnold
(74) *Attorney, Agent, or Firm* — Skaar Ulbrich Macari, P.A.

(57) ABSTRACT

A method and apparatus for treatment of cancer is provided. The method can include systemic administration of selective A3 adenosine receptor (A3AR) agonists like CI-IB-MECA (CF 101), LI-529, cordycepin or similar drugs in combination with application of pulsed Electric Field Stimulation (EFS) to the treatment area. A3AR agonists may be delivered in blend with allosteric enhancers of A3AR agonists potency like LUF6000 or other similar drugs. EFS is provided in three or more directions, which significantly increases expression of A3ARs on the cellular membranes and allows achieving a downstream apoptotic signal several-fold stronger than the signal created by an agonist alone. The apparatus may be dedicated to one patient usage over long period of time—hours and days continuously or intermittently.

10 Claims, 10 Drawing Sheets

METHOD AND APPARATUS FOR CANCER TREATMENT

FIELD

The invention relates to a method and apparatus for treatment of cancer using selective agonists of A3AR in combination with pulsed EFS. More specifically, it relates to enhancement of the natural ability of the body to cause death to cancer cells through activation of A3AR apoptotic signaling pathways, particularly the pathways associated with P53 gene, NF-κB and Wnt Signaling Pathway.

BACKGROUND

Cancer is a group of diseases involving abnormal cell growth with the potential to invade or spread to other parts of the body. Over 100 types of cancers affect humans. The most common types of cancer in males are lung cancer, prostate cancer, colorectal cancer and stomach cancer. In females, the most common types are breast cancer, colorectal cancer, lung cancer and cervical cancer. In the United States, more than 1.7 million cases of invasive cancer are diagnosed and more than 600,000 cancer related deaths happen each year. Under current estimates, two in five people will have cancer at some point in their lifetime. The financial cost of cancer is estimated to be more than $1.2 trillion USD per year. In spite of all efforts, the death toll from the major types of cancer has not significantly changed over the last decades.

There are three major methods of conventional cancer treatment: surgery, chemotherapy and radiation therapy. Surgery is effective in removing early-stage tumors and is useful in debulking large tumors. The main disadvantage of surgical treatment is its inability to kill cancer cells dispersed around the edges of the primary tumor and in the metastases spread across the body.

Radiation therapy is the use of ionizing radiation to kill cancer cells and shrink tumors. Ionizing radiation works by damaging the DNA of cancerous cells leading to their death. The disadvantages of radiation therapy include radiation damage to surrounding tissues, inability to kill all cancer cells in large tumors and existence of a limit for maximum delivered dose in one site that forbids using radiation therapy for recurrent treatments.

Chemotherapy is the use of anticancer drugs designed to slow or stop the growth of rapidly dividing cancer cells in the body. Surgery and radiation therapy remove or kill cancer cells locally in the targeted area, whereas chemotherapy works throughout the whole body and is able to kill both the prime and metastatic tumors. The major disadvantage of chemotherapy is its low selectivity to cancer cells, which leads to heavy damage to normal tissues that contain continuously dividing cells like skin, hairs, gut lining, etc.

Regretfully, it looks like all existing modalities—surgery, chemotherapy and radiation therapies have largely exhausted their therapeutic potentials and are unlikely to be the basis for significant improvements in cancer treatment.

Recently, a new understanding of cancer biology was introduced, which is referred to as "Cancer Stem Cell" (CSC) theory. The theory is supported by a significant body of experimental evidence and already accepted by the mainstream scientific community. The core concept of the theory is that each cancer tumor has a majority of differentiated cancer cells which are relatively passive, and a minority of CSCs which are highly active and solely responsible for tumor initiation, metastasis, resistance to conventional therapies and relapses. The CSC theory maintains that the cancer stem cells have better protection from harmful chemicals and better mechanisms of repair than the differentiated cancer cells. As a consequence, radiation and chemotherapy cannot efficiently kill CSCs and succeed in complete curing of cancer. For a therapy to cure cancer it must be able to efficiently kill both the differentiated cancer cells and CSCs.

In spite of a wide spread pessimistic view on the ability of existing therapies to cure major cancers, there is a reason for optimism. This reason is a recently discovered new natural mechanism of fighting cancer. The newly discovered mechanism allows a cell to check itself for being cancerous, and if it is, destroy itself by triggering apoptosis (programmed cell death). The name of the mechanism is A3AR apoptotic pathway (A3 Adenosine Receptor Apoptotic Pathway). The pathway senses concentration of free adenosine outside the cell by A3AR receptors, transduces the signal into the cell and, if the signal is significantly stronger-than-normal, the cell identifies itself as cancerous and launches a sequence of apoptosis that causes its own death. For reference: in normal tissues, extracellular adenosine concentration varies from 20 to 200 nM, whereas in cancerous tumors it could be as high as 30 μM. Triggered by A3ARs intracellular signal, apoptosis in cancer cells is executed by activation of gene P53 or another apoptotic pathway like WNT or NF-κB.

It is well known that cancer cells require a large amount of energy which they use for continuous division and proliferation. All cells consume energy from the intercellular space in form of glucose and convert it into ATP (Adenosine Triphosphate) within mitochondria of the cells. ATP is known as the intracellular "energy currency" that fuels the whole cellular machinery. ATP consists of one molecule of Adenosine and Three Phosphate groups. Every enzymatic biochemical reaction in a cell requires "phosphorylation"—a launching process in which an ATP molecule transfers to the reactant protein a phosphate group that carries the energy necessary for the reaction. After releasing all its 3 phosphate groups, the ATP is reduced to a free adenosine molecule. Through passive and active channels in the cellular membrane the adenosine molecules diffuse outside the cell, making the concentration of adenosine in the immediate environment of the cell approximately equal to the intracellular level. It is important that the concentration of free adenosine follows the energy consumption of the cell: the higher consumption—the higher concentration of free adenosine, both inside and outside the cell. By monitoring concentration of adenosine outside the cell with A3 adenosine receptors, the A3AR pathway can identify cancer cells by their higher-than-normal energy consumption and destroy them via apoptosis. Apoptosis involves activation of a group of proteases called "caspases" and a complex cascade of events that links the initiating stimulus of the high adenosine concentration outside the cell to its final demise. In other words, the A3AR apoptotic pathway serves as an autocrine/paracrine signaling loop that controls energy consumption of a cell and, if it significantly exceeds the normal physiological level, causes its self-destruction via apoptosis.

The A3AR Apoptotic Pathway is a natural cellular protector from cancer, and has become a subject of intense research only recently. Particular, it should be emphasized that the normal cells are refractory to the action of adenosine—A3AR apoptotic pathway. The ability of A3AR apoptotic pathway to cause death to cancer cells without damaging normal cells has immense therapeutic potential.

In US Patent Application Publication No. US2019/0299019 A1, which is hereby incorporated herein by reference in its entirety, a scanning apparatus for treatment of cancer tumors of different shapes and locations is disclosed. In the disclosed apparatus, a three-dimensional electric field stimulation (3D EFS) is provided by incorporating in the PEMF applicator three electromagnetic coils positioned spatially in such a manner that in the treatment zone they induce orthogonal to each other electric fields. Energized in a sequence, these coils deliver 3D EFS to the treatment zone. The scanning apparatus is universal, it is capable of delivering intense EFS to any location of prime and metastatic tumors in the human body.

In spite of all merits of the universal scanning apparatus, in many cases of treatment a simple and relatively low-cost versions of 3D EFS apparatus is needed. It may be used for an individual patient in his/her bed for treatment of one treatment zone continuously or intermittently for many hours and days.

Thus, there is a need in developing a simple and efficient cancer therapy device with the 3D EFS capabilities for cancer treatment.

SUMMARY

Provided herein is an efficient method of treatment of cancer with little or no side effects, as well as an apparatus for delivering cancer treatment to a patient.

Another objective is to provide a simple PEMF based apparatus dedicated for delivering 3D EFS for a long time to a single treatment zone of a patient.

Yet another objective is to provide an apparatus for delivering direct EFS to a patient by application of electric pulses directly to the treatment zone.

The novel method of treatment of cancer can be performed by combining systemic delivery of A3AR selective agonists like CI-IB-MECA, LI-529, cordycepin or similar drugs with 3D EFS of the treatment area. A3AR selective agonists may be delivered in combination with allosteric enhancers of efficiency of A3AR agonists. EFS is delivered in three or more directions, which significantly increases expression of A3ARs on the cellular membranes of cancer cells and allows achieving the downstream apoptotic signal several-fold stronger than the signal achieved with A3AR agonists alone. A3AR receptors and the P53 gene are functionally connected: when the downstream A3ARs signal reaches the P53 gene, it activates production of the p53 protein which launches a biochemical sequence that causes apoptosis of the cancer cell. Aside from the P53 gene, in some types of cancer, A3AR activation has been observed to cause disruption of the WNT or NF-κB signaling pathways that also leads to apoptotic demise of the cell.

A several-fold increase in the apoptotic signal required for curative cancer treatment is a challenging task. A simple rise of the amplitude of one-dimensional stimulation will not solve the problem because of two reasons: inherent saturation of the stimulating effect with the amplitude increase and the existence of a limit to the amplitude of electric pulses of about 50 mV/cm at which the electric field starts producing significant side effects: excitation of nerves and twitching of muscles in the treatment area. In this patent application the apoptotic signal is increased by employing a three-dimensional EFS. The possibility of enhancement of the apoptotic signal with three-dimensional EFS stems from the fact that adenosine receptors are tethered to the cytoskeleton and do not drift along the surface of the lipid cellular membrane. Also, in solid tumors the cancer cells do not rotate and keep constant their angular position relatively to the vector of the applied electric field. These two conditions lead to activation of A3ARs by one-dimensional EFS only on the side of the cell here the cellular membrane is normal to the applied electric field, whereas the full translocation of the A3ARs on the cellular membrane and associated with it increase in the apoptotic signal is achieved by employing a multidirectional, for example, 3D EFS.

When an electric field is applied to a cell, a transient process of about one microsecond duration is taking place. During this process the electric field is pushed out of the electrically conductive cytosol (Faraday cage effect) and is concentrated in the dielectric lipid membrane. In the part of membrane where the EF is normal to it, the electric field is amplified approximately 1000 times (ratio of the cell size and the thickness of the membrane) to a relatively high value of several V/cm, whereas at the "equator" of the cell, where the membrane is parallel to the applied field, the normal to the membrane component of the electric field is equal to zero. It means that translocation of the A3AR receptors to the surface of the membrane causing increase of expression of A3AR receptors happens only in the part of the membrane where the EF is strong and normal to the membrane. At the "equator" of the cell there is no EF normal to the membrane and hence no translocation of the receptors to the cell surface.

Accordingly, A3ARs are translocated to the surface by one dimensional EFS only in a part of the membrane. After translocation the receptors become active and ready to bind with adenosine or agonist drugs. In the rest of the membrane the receptors are not translocated to its outside surface and stay docked under the membrane in inactive "stand by" state.

To translocate the receptors in the equatorial area to the membrane surface and make them active, the stimulating electric field should be applied normally to these areas of membrane, for example, in two or more additional directions orthogonal to the vector of the previously applied EF. Additionally, switching polarity of the stimulating electric field allows doubling the number of active receptors on the cell. In short, to achieve a required several-fold increase in expression of A3ARs on the membrane, the cells should be stimulated by a pulsed electric field at least in 3 orthogonal directions with switching polarities.

In the apparatus disclosed in this application a three-dimensional EFS is achieved by a novel PEMF applicator in which four electromagnetic coils are arranged in one plane. A unique computer-controlled pattern of switching directions of electric currents in these four coils provides a 3D EFS pattern with a maximum at the center of the PEMF applicator. The disclosed applicator does not have "dead zones", it is relatively simple and inexpensive and can be designated to treatment of individual patients in their beds continuously or intermittently for a long period of time.

The disclosed method of cancer treatment includes systemic delivery of adenosine agonists of A3ARs in well-tolerated doses combined with local 3D EFS that increases the potency of drugs at the tumor site. The 3D EFS increases expression of A3ARs on cellular membranes that results in a several-fold amplification of the downstream apoptotic signal that leads to death of cancer cells, both differentiated and CSC.

The disclosed method of treatment can be applied at any stage of the disease. Also, it does not produce detrimental side effects and can be applied for a long time in one treatment site continuously or intermittently.

An intelligent controller is coupled to four-coil applicator and configured to control energizing each of the four coils during treatment.

Another implementation of a relatively simple low-cost apparatus for 3D EFS treatment of individual patients is also disclosed. It comprises a set of conductive electrodes applied directly to the patient's skin in strategically selected locations around the tumor and provides direct EFS to the treatment area in three or more directions. In this embodiment, EFS is provided directly from the electrodes without magnetic-to-electric field conversion used in the version of the PEMF apparatus with four-coil applicator. At least three pairs of electrodes are employed in this version of invention. The electrodes can be attached directly to the patient's skin with a conductive gel or a pressure sensitive conductive adhesion that provide reliable electric and mechanical contact between the electrodes and the skin near the treatment zone.

Direct EFS can be provided in the form of rectangular voltage pulses applied to the set of electrodes with duration in the range of 10 μsec to 10 msec. It also can be delivered by a sinusoidal electric signal continuous or pulsed. The range of stimulating frequencies in this case can be from 5 Hz to 250 kHz. The upper frequency should be at least several times less than the frequency defined by the time of relaxation of the cell which is about 1 MHz.

The direct EFS apparatus requires attachment of electrodes to the patient's skin around the tumor, which is an obvious drawback of the device in comparison with PEMF applicators that can act without direct contact with the patient body even through his/her clothing. However, the direct EFS apparatus has important advantages: the simplicity of its design and operation and a very low cost that makes it affordable for small hospitals and clinics where the apparatus can be provided to every single patient.

Another embodiment of the current invention is the administering A3AR agonists in combination with allosteric modulators that increase the maximal efficacy of the agonist-induced response.

Allosteric modulators are a group of substances that bind to a receptor and change receptor's response to stimulus. Allosteric refers to the binding sites that are different from the orthosteric primary ligand-binding site to which ligands such as endogenous adenosine and synthetic agonists bind. The binding of the allosteric modulators results in conformational changes of the receptor that affect binding of the orthosteric ligand with consequences for receptor affinity and efficiency.

Among allosteric compounds developed as 1H-imidazo[4,5-c]quinolin-4-amine derivatives compound LUF6000 significantly and selectively enhances agonist binding and function of A3 receptors. LUF6000 increases the maximum efficacy of A3 receptors agonists by an astonishing 45%!

The disclosure includes a pulsed electric field stimulation (EFS) apparatus for treatment of cancer. An applicator defines a common plane. A first electrical coil is provided to the applicator in the common plane, a second electrical coil is provided to the applicator in the common plane, a third electrical coil is provided to the applicator in the common plane, and a fourth electrical coil is provided to the applicator in the common plane. A controller electrically coupled to each of the first, second, third and fourth coils is configured to perform a first EFS pulse where the first and second electrical coils have a counterclockwise current while the third and fourth coils in have a clockwise current, perform a second EFS pulse where the first and third electrical coils have a counterclockwise current while the second and fourth coils have a clockwise current, and perform a third stimulation pulse where the first and fourth electrical coils have a clockwise current while the second and third coils in have a counterclockwise current.

The controller can also be configured to perform a fourth EFS pulse where the first and second electrical coils have a clockwise current while the third and fourth coils in have a counterclockwise current, perform a fifth EFS pulse where the first and third electrical coils have a clockwise current while the second and fourth coils in have a counter clockwise current, and perform a sixth stimulation pulse where the first and fourth electrical coils have a counterclockwise current while the second and third coils in have a clockwise current.

The applicator can include two layers of fabric. The first, second, third and fourth coils can be disposed between the two layers of fabric.

Each of the first, second and third electrical stimulation pulses can be rectangular pulses with a voltage amplitude in the range of 24V to 250V. The pulses can have a duration in the range of 5 μs to 1000 μs. The pulses can be separated by a time delay so that the first, second and third electrical stimulation pulses do not overlap one another. An electric current maximum in each of the first, second, third and fourth coils can be in the range of 200 A to 1000 A. A magnetic inductance in each of the first, second, third and fourth coils can be in the range of 5 mT to 50 mT.

The controller can be configured to repeat the first electrical stimulation pulse a plurality of times before performing the second electrical stimulation pulse. The controller can be configured to apply a plurality of the first, second and third electrical stimulation pulses sequentially.

The disclosure also includes a pulsed electric field stimulation (EFS) apparatus for treatment of cancer that includes a first pair of electrodes provided to a patient along a first of three mutually orthogonal axes, a second pair of electrodes provided to a patient along a second of the three mutually orthogonal axes, and a third pair of electrodes provided to the patient along a third of the three mutually orthogonal axis. A controller is electrically coupled to each of the first, second and third pairs of electrodes to generate three dimensional EFS along each of the first, second and third orthogonal axes.

The controller can be configured to energize two of the first, second and third pairs of electrodes to generate a stimulating electric field along axes different than the first, second and third orthogonal axes. The controller can be configured to energize each of the first, second and third pairs of electrodes to provide an electric field strength in a treatment area containing the cancer in a range of 10 to 50 mV/cm. The controller can be configured to energize each of the first, second and third pairs of electrodes via a sinusoidal signal.

The disclosure additionally includes a method of treating a cancerous tumor in a patient. An A3AR agonist is administered to the patient. Allosteric enhancers are administered to the patient simultaneously with the A3AR agonist. After administering the A3AR agonist and allosteric enhancers, EFS is provided to the cancerous tumor in at least three different directions to increase expression of A3ARs on a surface of cells of the tumor.

The EFS can be provided by applying an applicator to the patient. The applicator can define a common plane and include in that common plane a first electrical coil, a second electrical coil, a third electrical coil, and a fourth electrical coil. A first EFS pulse is performed where the first and second electrical coils have a counterclockwise current while the third and fourth coils in have a clockwise current. A second EFS pulse is performed where the first and third electrical coils have a counterclockwise current while the second and fourth coils in have a clockwise current. A third stimulation pulse is performed where the first and fourth electrical coils have a clockwise current while the second and third coils in have a counterclockwise current. Each of the first, second and third EFS pulses can be performed sequentially.

A fourth EFS pulse can be performed where the first and second electrical coils have a clockwise current while the third and fourth coils have a counterclockwise current. A fifth EFS pulse can be performed where the first and third electrical coils have a clockwise current while the second and fourth coils have a counterclockwise current. A sixth stimulation pulse can be performed where the first and fourth electrical coils have a counterclockwise current while the second and third coils have a clockwise current.

The EFS can also be provided by applying a first pair of electrodes provided to a patient along a the first axis of three mutually orthogonal axes, applying a second pair of electrodes provided to a patient along a second of the three mutually orthogonal axes, and applying a third pair of electrodes provided to the patient along a third of the three mutually orthogonal axes. The first, second and third pairs of electrodes can be energizing selectively to generate three dimensional EFS along each of the first, second and third orthogonal axes.

Two of the first, second and third pairs of electrodes can be energizing selectively to generate a stimulating electric field along an axis different than the first, second and third orthogonal axes.

The detailed description of the therapy and preferred embodiments for the invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIGS. 8A, 8B and 8C are schematic representations of sequential EFS along each of axes X, Y and Z, respectively.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various example embodiments; nevertheless, these example embodiments are not intended to limit the present invention to any specific example, embodiment, environment, application, or particular implementation described herein. Therefore, descriptions of these example embodiments are only provided for purpose of illustration rather than to limit the present invention.

Figure 1:
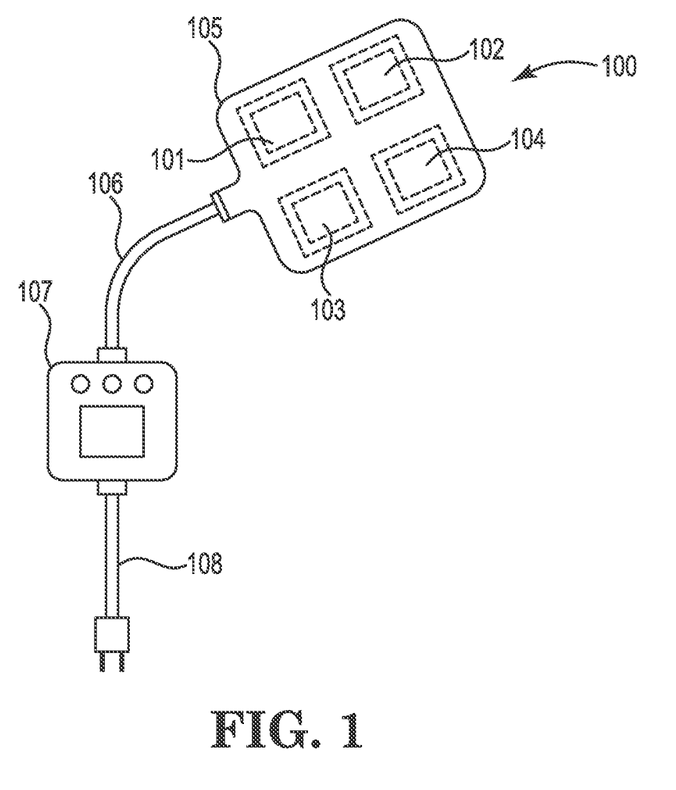
FIG. 1 is a schematic representation of EFS apparatus with a four-coil applicator having 3D electric stimulation capabilities.

An EFS apparatus 100 for treatment of a single target zone is depicted in FIG. 1. It comprises four electromagnetic coils 101, 102, 103 and 104 secured inside flat applicator 105. The applicator 105 comprises two layers of fabric, front and back, which enclose the coils and include multiple wires (not shown in the FIG. 1) that connect all four coils via cable 106 to computerized controller 107. A power cable 108 for powering the whole apparatus 100 is connected to a power source such as a wall power outlet or a battery. Exemplary, all four coils are rectangular, but other shapes also can be employed.

Applicator 105 can be efficiently used not only for cancer treatment but also as a general PEMF applicator intended for 3D EFS of kidneys for treatment of diabetic nephropathy, treatment of osteoarthritic joints and other applications.

Figures 2A, 2B:
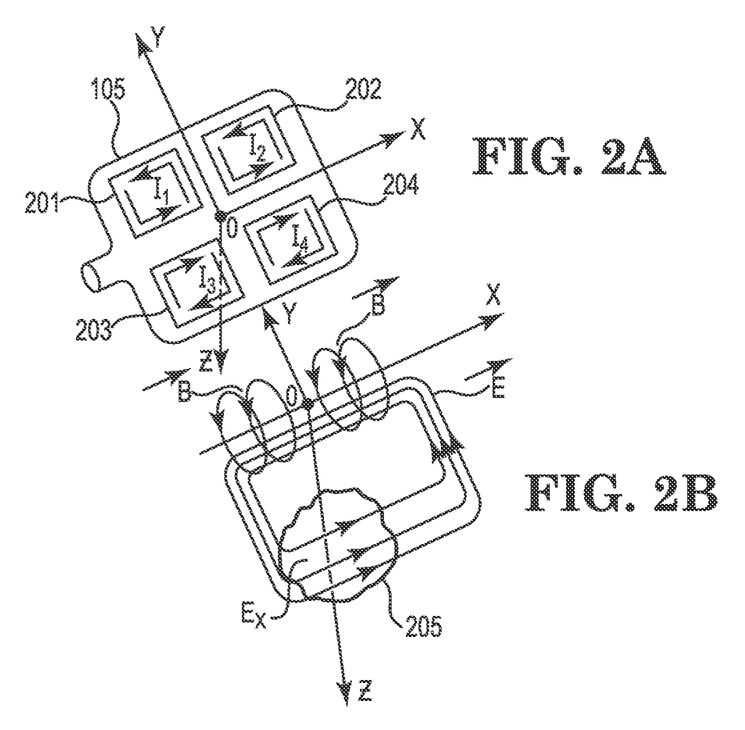
FIGS. 2A and 2B are schematic illustrations of a stimulating electric field generated in a first direction (X) in the treatment zone.

FIGS. 2A-2B schematically illustrate the process of generating EFS in the treatment zone by applicator 105 in one direction—parallel to axis X. In FIGS. 2A-4B, the applicator 105 is shown with a system of coordinates XYZ, where axis X is directed along applicator 105, axis Y—across applicator 105 normally to axis X, both in-plane of applicator 105, and axis Z perpendicular to the plane of applicator 105.

During a treatment session, applicator 105 is positioned flat on the patient's skin directly over the tumor 205 with axis Z crossing the tumor's center. The electric currents in coils 201, 202, 203 and 204 are designated by letters I1, I2, I3 and I4 with arrows showing directions of the currents. The currents in the sides of all four coils closest to the X-axis are directed along axis X. As shown in the FIG. 2A this corresponds to counter clock currents in coils 201 and 202 and clockwise currents in coils 203 and 204. FIG. 2B illustrates magnetic field B and electric field E generated by applicator 105 with designated directions of currents in the coils. The magnetic field B generated by coils is axially symmetric around axis X. The electric field E is generated by the changing magnetic field B. In FIGS. 2A-4B, magnetic field B is increasing which defines the direction of the vector of field E. The field E is curled with its lines locked on themselves. At the tumor 205 lines $E_x$ of the stimulating electric field are parallel to axis X.

Figure 3A:
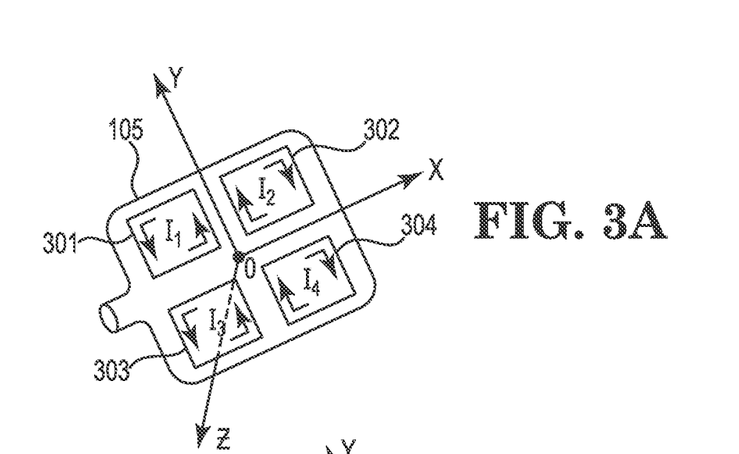
FIGS. 3A and 3B are schematic illustrations of a stimulating electric field generated in second direction (Y) in the treatment zone.
Figure 3B:
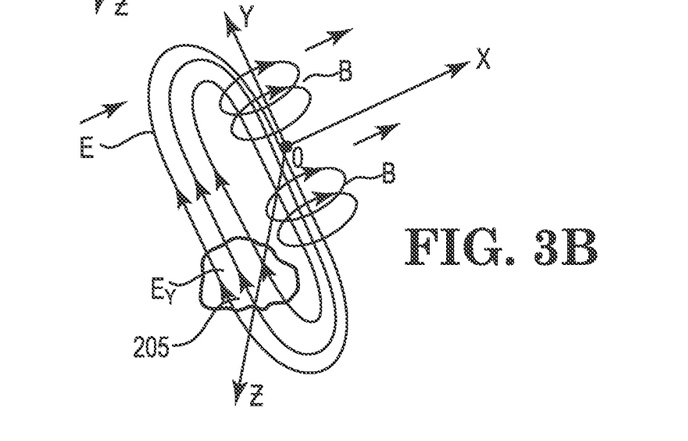

FIGS. 3A-3B schematically demonstrate the process of generating EFS in the treatment zone by applicator 105 in the second direction—parallel to axis Y. In this case the currents in the sides of all four coils closest to the axis Y are directed along the axis Y. The electric currents in coils 301, 302, 303 and 304 are designated by letters I1, I2, I3 and I4 with arrows showing directions of the currents (FIG. 3A). As shown in the FIG. 3A, this corresponds to counterclockwise currents in coils 301 and 303 and clockwise currents in coils 302 and 304. FIG. 3B illustrates magnetic field B and electric field E generated by applicator 105 with designated directions of currents in the coils. In FIGS. 3A-3B the magnetic field B generated by coils is axially symmetric around axis Y. At the tumor 205, lines $E_y$ of the stimulating electric field are parallel to the axis Y.

Figures 4A, 4B:
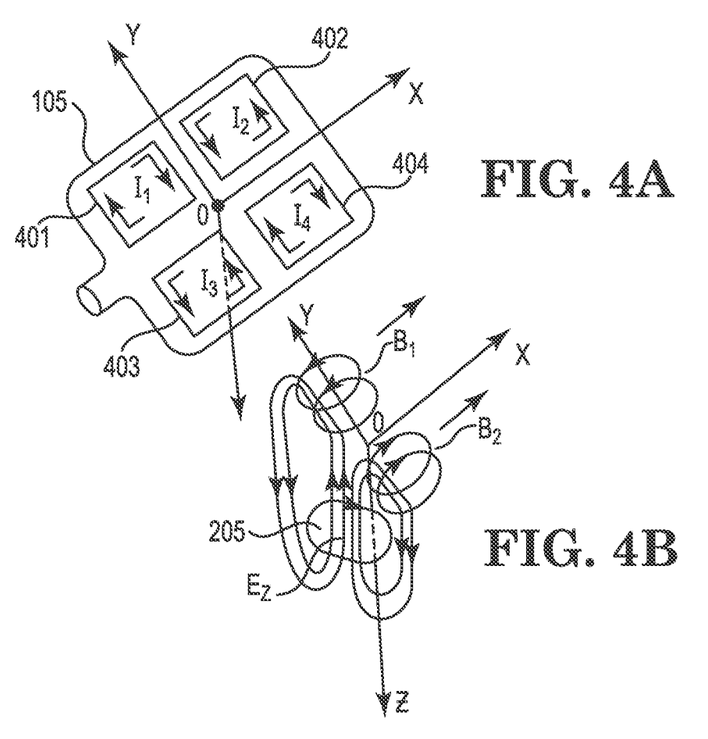
FIGS. 4A and 4B are schematic illustrations of a stimulating electric field generated in third direction (Z) in the treatment zone.

FIGS. 4A-4B schematically demonstrate the process of generating EFS in the treatment zone by applicator 105 in the third direction—parallel to axis Z and normally to the applicator plane. In this case the currents in the sides of two coils closest to the Y-axis are directed along the axis Y and in the other two coils closest to the Y-axis—in opposite directions as shown in FIG. 4A. This corresponds to clockwise currents in coils 401 and 404 and counterclockwise currents in coils 402 and 403. FIG. 4B illustrates magnetic field B and electric field E generated by applicator 105 with designated directions of currents in the coils. In FIGS. 4A-4B the magnetic field B generated by coils is axially symmetric around axis Y. At the tumor 205 lines $E_z$ of the stimulating electric field are parallel to the axis Z and normal to the plane of applicator 105.

By changing the directions of the currents in coils the magnetic field can be generated symmetrically around axis X, which also produce EFS along axis Z normal to the plane of the applicator 105.

In the process of a treatment session each pattern of distribution of the currents in coils 101, 102, 103 and 104 is activated sequentially as shown in FIGS. 2A-4B. Additionally, the directions of current in each pattern may be switched to the opposite, which makes EFS twice as efficient. Operating in this manner the apparatus 100 provides 3D EFS to the tumor cells with high intensity and without "dead zones" in the treatment volume (also referred to as the "treatment zone") that contains the tumor.

Figure 5A:
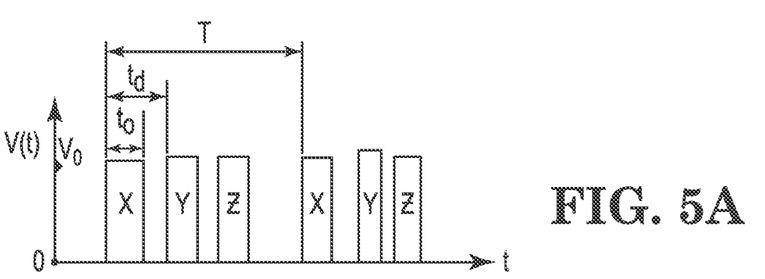
FIGS. 5A, 5B and 5C are a series of time diagrams of voltage applied to the coils (A), electric current and magnetic field in coils (B) and stimulating electric field in the treatment zone (C).

FIG. 5A shows a time diagram of voltage pulses applied to the coils. The controller 107 supplies the coils 101-104 of the applicator 105 with a series of rectangular pulses marked X, Y, and Z. The pulses may have amplitude $V_0$ ranging from 24V to 250V, duration $t_0$ between 5 µs to 1000 µs and frequency f (f=1/T) from 2 Hz to 250 Hz, where T is the period between two consecutive series of pulses. The pulses in the sequence are delayed by time $t_d$ that is longer than duration of pulses $t_0$, so they do not overlap.

Figure 5B:
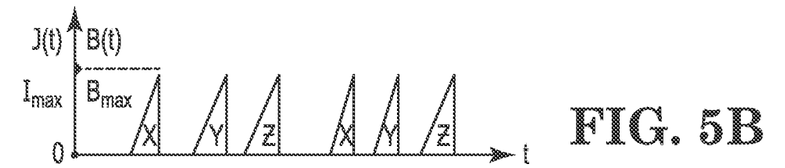
Figure 5C:
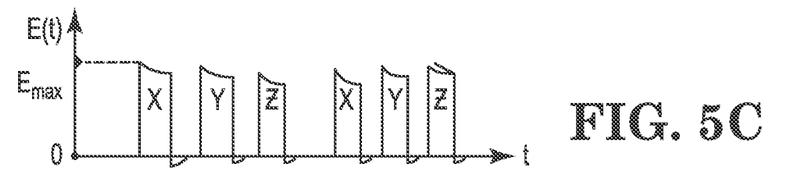

The diagram of FIG. 5B shows the electric current I(t) and magnetic field B(t) in the coils. An exemplary value of maximum current $I_{max}$ is 200 A to 1000 A, and a value of magnetic inductance lies in the range of 5 mT to 50 mT. The diagram represents ascending exponential curves close in shape to a straight line. The diagram of FIG. 5C further depicts the pulsed electric field in the treatment zone with amplitude Emax equal to 10-50 mV/cm.

In another implementation of the apparatus, the controller 107 may supply the coils of applicator 105 with voltage pulses sequence X, X, X for several seconds or minutes, then a series of pulses Y, Y, Y and a series of pulses Z, Z, Z.

Figure 6:
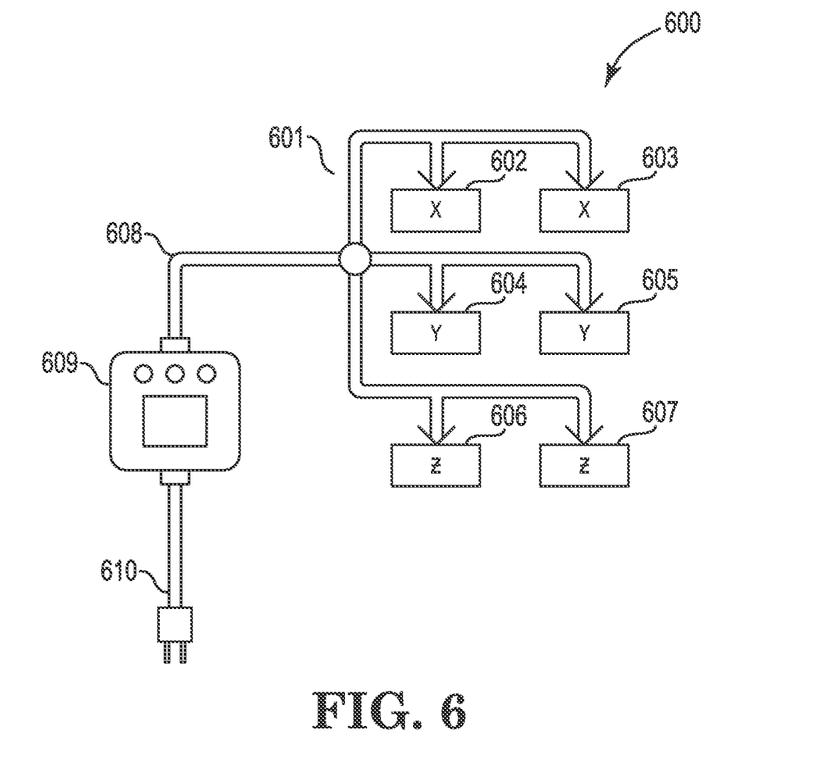
FIG. 6 is a schematic representation of an apparatus for direct 3D EFS stimulation.

FIG. 6 schematically illustrates another embodiment of present invention—a system 600 for direct 3D EFS. This embodiment does not utilize electromagnetic coils for conversion of magnetic field into the stimulating electric field. Instead, it delivers electric pulses directly to the electrodes positioned around the treatment zone thus providing EFS to the tumor. Applicator 601 for direct 3D EFS includes electrodes 602 and 603 for applying electric field along axis X, electrodes 604 and 605 for electric field stimulation along axis Y and electrodes 606 and 607 for electric field stimulation along axis Z. Multi-wire cable 608 connects the electrodes 602-607 to an intelligent controller 609 which is powered via cable 610 from the power grid, battery or other power source. During operation, controller 609 delivers a predetermined sequence of electric pulses to electrodes 602-607 to create in the treatment zone stimulating electric fields of different directions as discussed herein.

Figure 7:
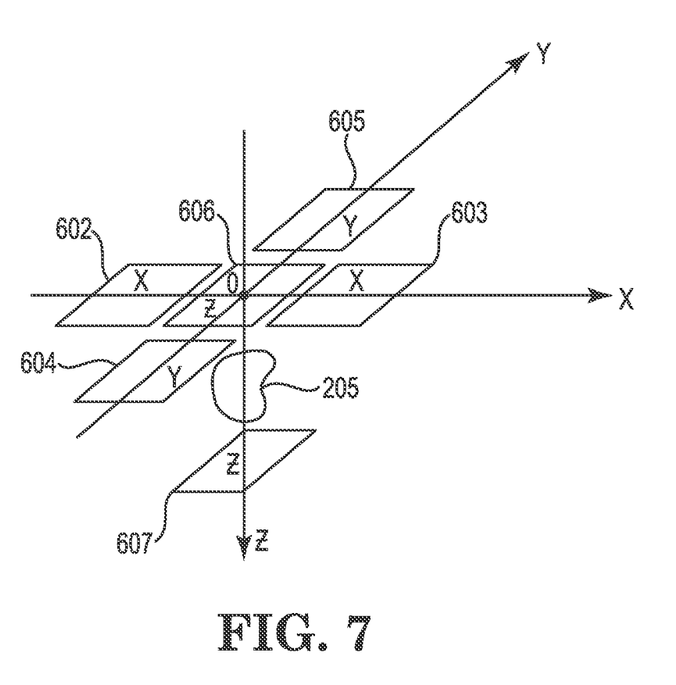
FIG. 7 is a schematic representation of an apparatus for direct 3D EFS with six electrodes positioned around the treatment zone.

FIG. 7 schematically illustrates an arrangement of electrodes 602-607 on the patient's skin around the treatment zone containing the tumor 205 to be treated. The center of the system of coordinates XYZ is positioned over the center of the tumor 205. With some separation, electrodes 602 and 603 are positioned along axis X, electrodes 604 and 605 along axis Y, and electrodes 606 and 607 directly over and under the tumor 205 along axis Z.

Figure 8A:
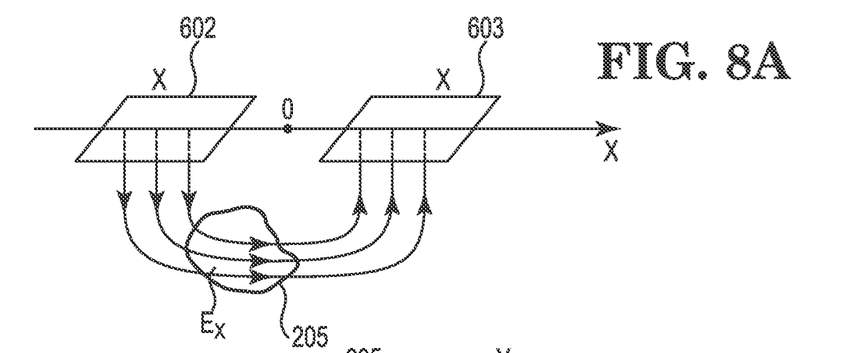
Figure 8B:
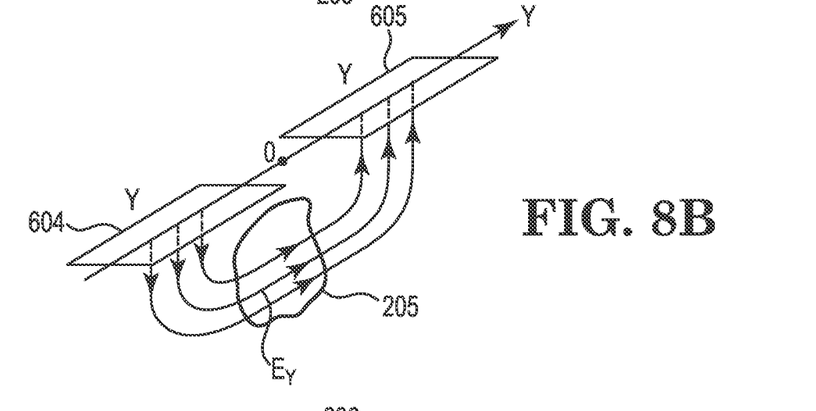
Figure 8C:
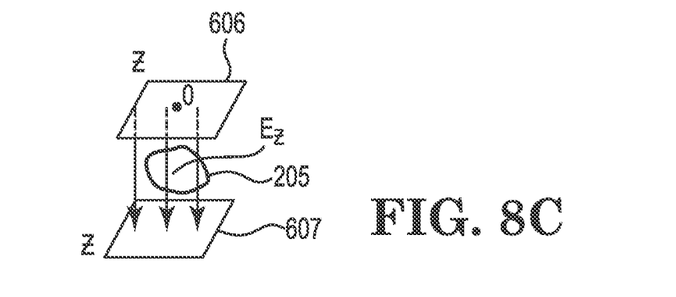

FIGS. 8A, 8B and 8C illustrate 3D EFS of the tumor 205 by consecutive applications of voltage pulses between electrodes 602 and 603, 604 and 605, and 606 and 607. As shown in FIGS. 8A-8C, these pulses applied to electrodes create stimulating electric fields $E_x$, $E_y$ and $E_z$ along axes X, Y and Z correspondingly.

The apparatus for direct EFS may provide not only 3D stimulation along the axes X, Y, Z but also along multiple axes directed at 45 degrees to the axes X, Y, Z. This can be done by application of stimulating electric fields to two axes simultaneously.

Figure 9:
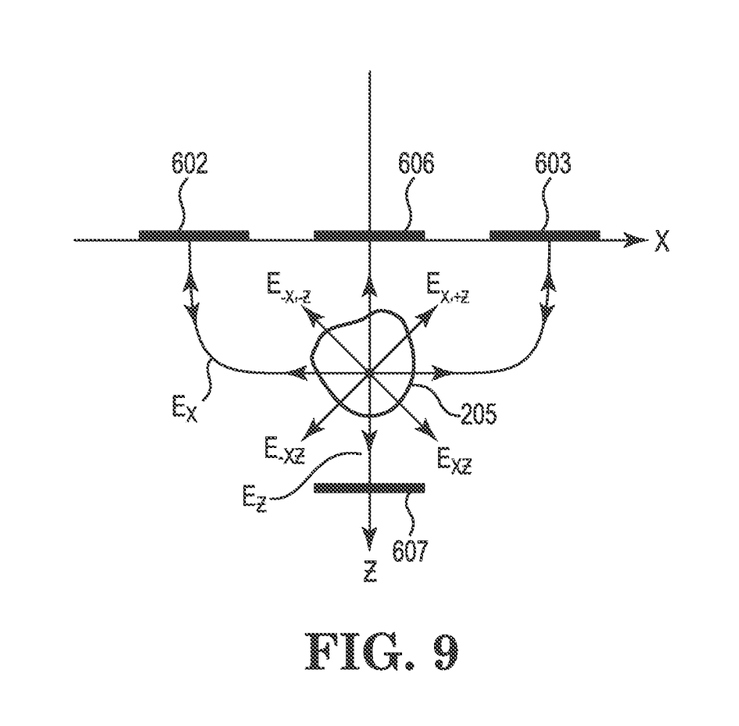
FIG. 9 is a schematic representation of EFS in the case of application of voltage pulses to two electrodes simultaneously.

FIG. 9 Illustrates this mode of EFS: application of electric pulses simultaneously to two different pair of electrodes: X and Z. FIG. 9 demonstrates 4 differently directed electric fields $E_{xz}$, $E_{x-z}$, $E_{-xz}$ and $E_{-x-z}$ in the XZ plain resulting from simultaneous application of electric fields along axes X and Z with positive and negative directions of the fields along the X and Z axes. Overall, the whole number of stimulating directions provided by the apparatus for direct EFS of the treatment zone is 18. This high number of directions of stimulating electric fields provides practically uniform stimulation of the whole cellular membrane and maximizes expression of A3ARs on the cellular membrane.

Figure 10A:
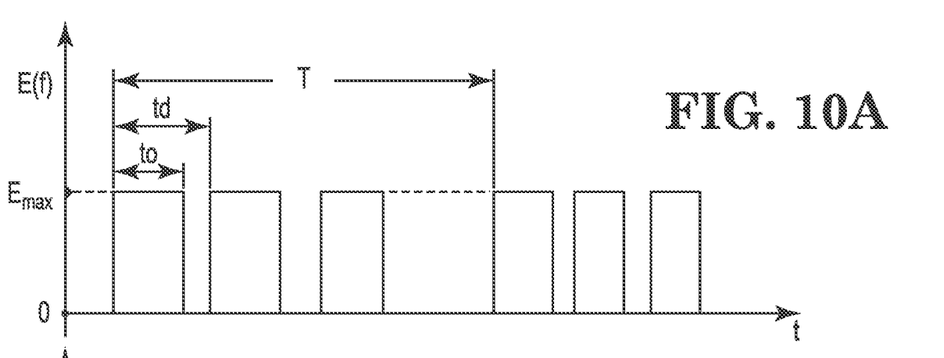
FIGS. 10A and 10B are time diagrams of voltage applied to the electrodes of apparatus 600 for direct EFS: rectangular pulses (A) and sinusoidal signal (B).

FIG. 10A provides a time diagram of electric pulses delivered by intelligent controller 609 to each pair of electrodes 602-603, 604-605, 606-607. Preferred electric pulses are rectangular with duration $t_0$ of 10-5000 µs, delay time $t_d$ selected to be longer than $t_0$, so the consecutive pulses do not overlap, and period between consecutive group of 3 pulses is T=1/f where f=5-1000 Hz. Polarity of the electric pulses on the diagram can be changed every 10-20 min. Also, the electric pulses can be applied to a pair of electrodes: XZ, XY and YZ simultaneously for creating EFS in all 18 directions. The amplitude of the electric pulses generated by the intelligent controller 609 and applied to electrodes is in the range of 0.5 V to 5 V. Depending of distances between the electrodes and the position of the tumor, it should provide electric field $E_{max}$ in the tumor ranging from 10 to 50 mV/cm.

An optimum way of selecting the treatment electric field $E_{max}$ for each pair of electrodes is to increase the applied voltage to the level of transcutaneous excitation of nerves causing twitching and decrease it by 10-20 percent to a comfortable level.

Figure 10B:
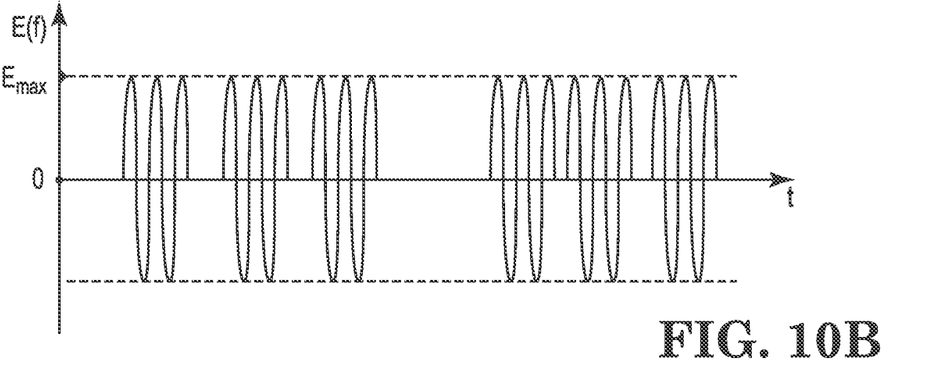

FIG. 10B illustrates an embodiment of the apparatus for direct EFS in which intelligent controller 609 provides the electrodes with not rectangular electric pulses, but instead sinusoidal signals both for electrodes for X, Y, Z stimulation as well as for pairs of electrodes for applying EFS in all 18 possible directions. The frequency of the sinusoidal signal can lay in the range of 5 Hz to 250 kHz.

In the method of cancer treatment, first of all, an A3AR agonist, exemplary, CI-IB-MECA is administered to the patient in well tolerable and efficient concentrations. CI-IB-MECA may be delivered simultaneously with allosteric enhancer LUF6000 whereas 3D EFS may start simultaneously with drugs delivery or with 0.25-0.5-hour delay.

Duration of EFS can be 1 to 4 hours per session, two-three sessions a day, seven days a week. It also can be continuous or intermittent for many days and weeks. Selection of the treatment schedule is at the physician's discretion. Because CI-IB-MECA, LUF6000 and EFS do not produce significant side effects, repetitive treatments can last for many weeks.

Adenosine is a primordial molecule that performs many vital biological functions in the body. One of them is being a carrier of energy by ATP, ADP and AMP that provide necessary energy for all biochemical reactions in the cellular machinery. Another important adenosine physiological function is that its concentration in the intercellular space serves as an indicator of energy consumption and is used by autocrine and paracrine signaling for controlling the energy balance in tissues. As an example, during inflammation the energy spending in tissues can be as high as 40 times of the base level. Acting through adenosine—A2AR anti-inflammatory signaling pathway, adenosine decreases energy consumption of all immune and parenchymal cells involved in the inflammatory process and keeps the energy consumption of inflamed tissue in the physiological limits.

Uncontrollably dividing cells in cancer tumors consume high amounts of energy and create a hypoxic and energy deprived state in tissue. In this case the high concentration of adenosine acts through the adenosine-A3AR anticancer signaling pathway and limits energy consumption in cancerous cells by inducing their apoptosis.

It should be mentioned that the cancer cells can be killed by activation of adenosine-A3AR pathway only if the pathway is completely viable. If the adenosine-A3AR pathway is compromised by mutations, the system of controlling cancer cells proliferation is broken and unchecked cell proliferation proceeds to full scale cancer. In many forms of cancer, though, the anticancer adenosine-A3AR pathway is disabled only partially and, as has been demonstrated in multiple studies, can be revitalized by administration of a significant dose of A3AR agonists like CL-IB-MECA. Regretfully, so far, this approach rendered only limited improvements: even though apoptosis induced by CL-IB-MECA slowed down the growth of cancer tumors, the apoptosis rate was lower than that of the cancer growth and the tumors continued to grow.

The major aspect of the current invention is that additional means, supplemental to the administration of A3AR agonists, are provided by administration of allosteric enhancers and application of 3D EFS to the treatment zone.

The 3D EFS raises the potency of the adenosine-A3AR apoptotic pathway by increasing expression of A3ARs on the cancer cells whereas the allosteric enhancer increases the efficiency of orthosteric A3AR agonists.

In several in vivo studies it was demonstrated that administration of A3AR agonist CL-IB-MECA causes apoptosis of cancer cells with a rate at least 50% (actually 52% to 79%) of the tumor growth rate. In another study it was shown that application of one-dimensional EFS increases the apoptotic rate caused by administration of CL-IB-MECA by factor of 0.4. Extrapolation of these results to the 3D EFS with two polarities in each dimension gives for the apoptotic rate a six-fold increase equal to 0.4×6×50%=120%. Together with the 50% of the apoptotic rate provided by the agonist alone it results in the total apoptotic rate 50%+120%=170% of the tumor growth rate. Allosteric enhancer LUF6000 can add additional 45% increase in the agonist efficacy, which leads to the total apoptotic rate of 246% of the tumor growth. Both apoptotic rates 170% and 246% are higher than the tumor growth rate and will lead to remission of the tumor. In other words, the combination of A3AR agonist with 3D EFS and with-or-without an allosteric enhancer promises a complete remission of the cancer tumor. The allosteric enhancer can be used for increasing efficiency of the treatment and shortening the treatment time. Keeping in mind that A3AR apoptotic pathway kills not only differentiated cancer cells but also CSCs, the complete remission of the tumor means a curative treatment.

Advantages of the disclosed Adenosine—A3AR cancer therapy are numerous: the therapy meets requirements of CSC theory to be able to kill both differentiated and CSCs. As a natural anti-cancer defense, it has no significant side effects: all normal cells are refractory to the therapy. During treatment EFS is uniformly applied along the tumor, its effectiveness does not depend on distances from capillaries as in the case of chemotherapy drugs. Contrary to chemotherapy and radiation treatments the Adenosine—A3AR therapy can be used for repeated treatments if a previously treated tumor relapsed. Also, it is a wide spectrum therapy capable of treating a number of major types of cancer: prostate, colon, lung, liver, pancreas, brain etc. It is applicable for early stages as well as advanced metastatic stages of cancer, for operable and not operable tumors.

Selective A3AR agonists used for therapy are not expensive, currently about $1000 per full treatment of one patient. Additional benefits of the therapy are the relatively low cost of the equipment and simplicity of the treatment.

Adenosine—A3AR cancer therapy can be beneficially combined with therapies that slow down the growth rate of cancer tumors: continuous or intermittent fasting, different regiments of calorie restriction, or angiogenesis inhibition-based therapies.

While the invention has been described in connection with what is presently considered to be the most practical and preferred example embodiments, it will be apparent to those of ordinary skill in the art that the invention is not to be limited to the disclosed example embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

It is also within the scope of the invention to combine features, functions, advantages and aspects of the various embodiments described herein. Thus, the embodiments of the invention may comprise combinations of aspects of any one or more of these exemplary embodiments.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A pulsed electric field stimulation (EFS) apparatus for treatment of cancer, the apparatus comprising:
an applicator defining a common plane, comprising:
a first electrical coil provided to the applicator in the common plane;
a second electrical coil provided to the applicator in the common plane;
a third electrical coil provided to the applicator in the common plane; and
a fourth electrical coil provided to the applicator in the common plane; and
a controller electrically coupled to each of the first, second, third and fourth coils,
wherein the controller is configured to:
perform a first EFS pulse where the first and second electrical coils have a counterclockwise current while the third and fourth coils have a clockwise current;
perform a second EFS pulse where the first and third electrical coils have a counterclockwise current while the second and fourth coils have a clockwise current; and
perform a third stimulation pulse where the first and fourth electrical coils have a clockwise current while the second and third coils have a counterclockwise current.

2. The apparatus of claim 1, the controller is configured to:
perform a fourth EFS pulse where the first and second electrical coils have a clockwise current while the third and fourth coils have a counterclockwise current;
perform a fifth EFS pulse where the first and third electrical coils have a clockwise current while the second and fourth coils have a counterclockwise current; and
perform a sixth stimulation pulse where the first and fourth electrical coils have a counterclockwise current while the second and third coils have a clockwise current.

3. The apparatus of claim 1, wherein the applicator comprises two layers of fabric, and wherein the first, second, third and fourth coils are disposed between the two layers of fabric.

4. The apparatus of claim 1, wherein each of the first, second and third electrical stimulation pulses are rectangular pulses with a voltage amplitude in the range of 24V to 250V.

5. The apparatus of claim 1, wherein each of the first, second and third electrical stimulation pulses are rectangular pulses with a duration in the range of 5 $\mu$s to 1000 $\mu$s.

6. The apparatus of claim 1, wherein each of the first, second and third electrical stimulation pulses are separated by a time delay so that the first, second and third electrical stimulation pulses do not overlap one another.

7. The apparatus of claim 1, wherein the controller is configured to generate an electric current maximum in each of the first, second, third and fourth coils in the range of 200 A to 1000 A.

8. The apparatus of claim 1, wherein the controller is configured to generate a magnetic inductance in each of the first, second, third and fourth coils in the range of 5 mT to 50 mT.

9. The apparatus of claim 1, wherein the controller is configured to repeat the first electrical stimulation pulse a plurality of times before performing the second electrical stimulation pulse.

10. The apparatus of claim 1, wherein the controller is configured to apply each of the first, second and third electrical stimulation pulses sequentially.

* * * * *